United States Patent [19]

Wind et al.

[11] 4,165,285

[45] Aug. 21, 1979

[54] COMBINED ANAEROBIC REACTOR AND SETTLER

[75] Inventors: Evert Wind, Houten; Robbert de Vletter, Huizen, both of Netherlands

[73] Assignee: N.V. Centrale Suiker Maatschappij, Amsterdam, Netherlands

[21] Appl. No.: 808,644

[22] Filed: Jun. 21, 1977

[30] Foreign Application Priority Data

Jun. 24, 1976 [NL] Netherlands .......................... 7606904

[51] Int. Cl.$^2$ .............................................. C02C 1/14
[52] U.S. Cl. .................................. 210/195.3; 210/197; 210/256
[58] Field of Search ..................... 210/2, 3, 4, 5, 6, 14, 210/16, 195 S, 195 SO, 197, 256, 261, 205, 207, 208; 195/108, 115, 127, 139, 144

[56] References Cited

U.S. PATENT DOCUMENTS

| | | | |
|---|---|---|---|
| 1,399,561 | 12/1921 | Imhuff | 210/4 |
| 2,174,203 | 9/1939 | Ducellier et al. | 195/144 |
| 2,889,929 | 6/1959 | Kivell | 210/4 |
| 3,236,384 | 2/1966 | Sontheimer | 210/197 |
| 3,459,659 | 8/1969 | Bedker | 210/3 |
| 3,495,711 | 2/1970 | Englesson et al. | 210/195 S |
| 3,617,544 | 11/1971 | Voss | 210/261 |
| 4,008,153 | 2/1977 | Mackrle et al. | 210/261 |

FOREIGN PATENT DOCUMENTS

| | | | |
|---|---|---|---|
| 233486 | 5/1974 | Austria | 210/256 |
| 2728585 | 12/1977 | Fed. Rep. of Germany | 210/195 S |
| 2030969 | 6/1978 | Fed. Rep. of Germany | 210/256 |

OTHER PUBLICATIONS

Toepassing van Methaangisting voor de Behandling van Minder Geconcentreerd Afvalwater, Lettinga and Velsen, H$_2$O, 1974, 7:281-289, Patent Office Rough Draft Translation of Toepassing van Methaangisting de Behandling van Minder Geconcentreerd Afvalwater.

*Primary Examiner*—Charles N. Hart
*Assistant Examiner*—Ernest G. Therkorn
*Attorney, Agent, or Firm*—Bucknam and Archer

[57] ABSTRACT

The invention relates to an installation for anaerobic purification of waste or effluent water comprising particles which comprises a reactor, an after-settler device in the top part of the reactor which separates an upper settling zone from an anaerobic decomposition zone, and means are provided for using the developed methane gas as a transport aid of the particles and for separating said gas from said particles.

12 Claims, 3 Drawing Figures

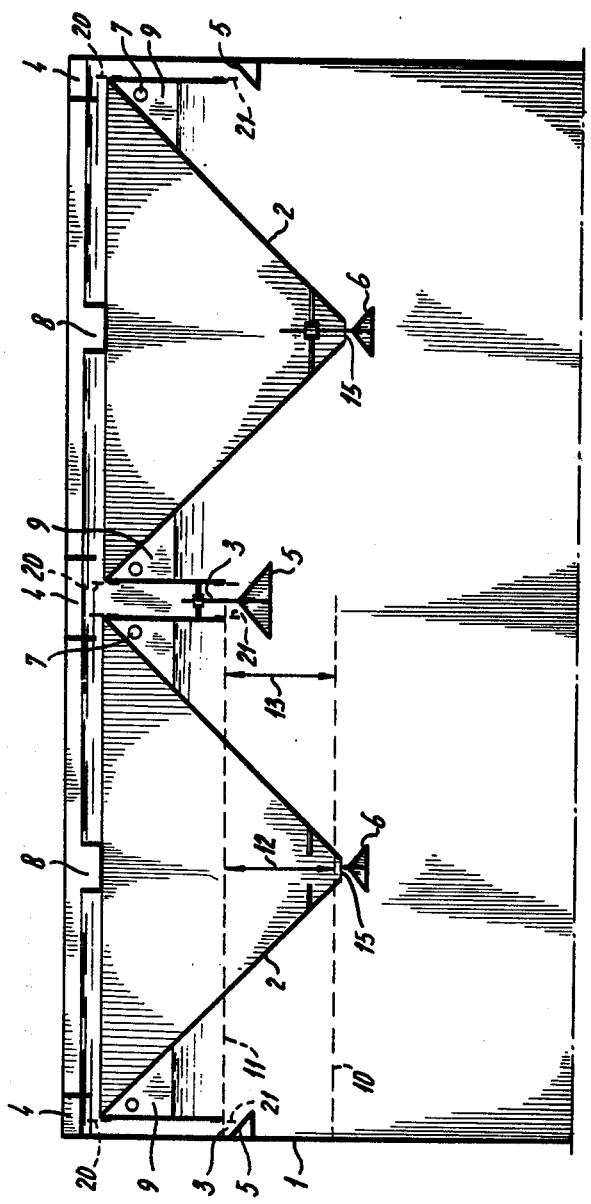

COMBINED ANAEROBIC REACTOR AND SETTLER

BACKGROUND OF THE INVENTION

The invention relates to an improved installation for the anaerobic purification of waste or effluent water comprising particles of decomposable impurities.

The installation comprises a reaction or decomposition zone into which waste water comprising a sludge of impurities is fed.

It is known, that waste water comprising decomposable organic substances can be purified by an anaerobic microbial decomposition process, whereby methane and carbon dioxide are being originated.

The use of this process for the straight purification of waste water, particularly of concentrated industrial effluent water has been tried, but it showed several disadvantages. A stable fermentation process can hardly be obtained, and a useful practice comparable with aerobic purification could not be realised in a technical scale. In the journal "H$_2$O" (1974), Nr. 7, pp. 281-289 the state of the art has been given, with a comprehensive literature reference.

It has been described in said publication, page 281, that in using a methane-developing fermentation for the treatment of less concentrated waste water (having 0.1 through 0.5% by weight of organic matter, one of the most important problems is to find a practically acceptable way for rinsing out the sludge. A stable methane-developing fermentation can be accomplished in a continuous way only if the total amount of active bacterial material in the reactor can be maintained at a constantly high level.

On page 283, FIG. 1 of said publication an experimental device is shown, wherein an after-settler-zone next to and at the top of a recipient for the interception of the gas is provided, said recipient at its lower side having a circular opening, which serves as the inlet as well as the outlet of the after-settler. With such a device a stable and continuous process cannot be achieved.

The problems reflected, which relate to the experiences as described with an experimental device having a contents of 16 liters are being still more severe with industrial reactors having a volume of dozens or several hundreds of cubic meters.

In the existing conventional sludge fermentation tanks e.g. a retention period of the entire mixture of about 30 days is a normal feature. For an efficient purification this sludge retention period (i.e. life-time of the sludge) might not be made shorter (at least 10 days, see the above publication, page 287 at the bottom), while at the same time the retention period of the liquid is reduced to several hours (viz. 3 through 6 hours). An effective purification can be achieved in such a short period only if relatively high concentrations of sludge are present in the reactor (i.e. dozens of grams per liter). In order to obtain this, an efficiently working system is necessary, wherein the following requirements are met:

1. The ascending gas bubbles are being collected, and the gas will be removed efficiently, such that no foam or liquid droplets will be entrained.

2. The liquid is separated from the mixture of sludge and liquid in such a way that a substantially sludge-free effluent will be produced.

3. The sludge separated from said liquid will be concentrated and be recycled into the reactor zone at the highest possible rate.

The separation of sludge and effluent in the conventional aerobic purification systems is in general carried out by means of an after-settler separate from the aeration zone, and the thickened-in sludge is recirculated into the aeration zone through a conduit by means of a pump if any or by other means.

Since in aerobic systems considerable sludge formation is obtained, part of the thickened-in sludge is cocurrently removed from the system (gutter sludge).

This is entirely different from anaerobic purification, for the following reasons:

a. In view of minor sludge formation only small amount of sludge has to be removed.

b. There is no need for using a sump of the after-settler in order to obtain a concentrated gutter sludge, since at the bottom of the reactor there exists a very high sludge concentration as a result of the good settling properties of the anaerobic sludge.

c. The retention period of the sludge outside the reactor ought to be restricted to a minimum, because otherwise gas formation and flotation might occur, such that the function of the settler device would become inefficient.

Several attempts to use anaerobic purification on industrial scale have failed, substantially for reasons of the issue mentioned in the last-above page.

It is an object of the present invention to comply with the requirements as mentioned in the above under 1 through 3, without occurrence of flotation and of other problems.

It is a further object of the present invention to obtain the following advantages:

Simple construction

Easiness of access to all constructional parts

Absence of moving constructional parts, including recycling pump devices

Possibility of an optimal adaptation of the installation to the typical properties of a certain envisaged type of waste water and of sludge, as well as to the input charge, by a proper selection of the mutual ratios of dimensions and by a control or adjustment of the inlet-opening or openings of the settler-device.

A continuous process.

Still another object of the present invention is to provide a compact efficient installation for the anaerobic purification of industrial and/or domestic waste waters or effluents.

Other objects will be elucidated by the specification in detail of the invention, by the Figures enclosed and by the claims.

DETAILED SPECIFICATION OF THE INVENTION

In order to comply with all the requirements mentioned in the above, use is made according to the present invention of the principle, that a column of a liquid in which gas-bubbles are present, will have a lower specific weight than a liquid without such bubbles.

This principle, upon which the known device of the mammoth pump is based, renders a number of specific advantages as well as disadvantages as compared with other types of pumps, and it is used only in special fields.

Surprisingly, it has been found according to the present invention that this principle can be used to transport the liquid from the anaerobic reactor zone into the after-settler compartment and to recycle the sludge back into the reactor, without an input of energy and without moving mechanical parts.

The installation for anaerobic purification of waste or effluent water, which installation comprises a reactor zone and a compartment for after-settling positioned therein and provided with a separating means for gases, sludge and liquid is characterized according to the present invention in that said after-settling compartment at the top of said reactor zone is separated therefrom and is provided with an inlet opening for the mixture of sludge and water from said reactor zone, with an outlet opening to said reactor zone, said outlet opening being positioned lower than said inlet opening, such that sludge separated by settling in said after-settling compartment is returned into said reactor zone, while conducting means are provided which shield the inlet openings from and the outlet openings to the after-settling compartment from the upward flow of developed gases, and separate means are positioned for interception and removal of said gases, such that continuously an amount of anaerobic sludge is being separated and recycled in order to have a purification process which proceeds by fermentation in a continuous and stable manner.

The installation is preferably provided with means for the control and adjustment of the height of the inlet openings of the after-settler.

The inlet opening into the after settler is positioned in top of a shielding bulkhead which conducts the ascending gas bubbles in a direction at the side of the horizontal projection of said inlet opening into the interception zone for same, while the liquid with sludge is allowed to flow around said bulkhead to the inlet opening.

The outlet opening at the bottom of the after-settling compartment is positioned higher than the bulkhead which is placed oblique or horizontally in the reactor zone and which prevents the ascending gas bubbles to reach the outlet opening.

Over the bulkhead is a vertical channel a vertical wall of which being substantially protruding into an overflow to the after-settler compartment, said wall under said overflow forming an intercepting zone with the wall of the after-settling compartment, wherein the gas is intercepted and from which the gas can be removed under controlled overpressure.

The after-settling compartment is widening in a conical way in the upward direction and it has at its top a zone to collect foam which is open at its lower side, and delimited by a wall, into which protrude one or several tubings, leading from that wall of said after-settling compartment in an oblique way upward until said delimiting wall, such that inlet openings are formed for the mixture of sludge and water to pass into said after-settling compartment.

The installation comprises adjustable means for the control of the height of the inlet opening for the mixture of sludge and water to pass into the after-settling compartment.

One or several tubes may be constructed in a sliding way movable along their longitudinal axis such that the height of the inlet opening from the reactor zone into the after-settling compartment at the end of said tubes protruding into said reactor zone may be varied in a controllable way said sliding tubes are positioned in fixed tubes which extend from the wall of the after-settling compartment to the wall of the foam collecting zone.

STATE OF THE ART

From German Patent Specification No. 275,498 an installation is known for the treatment of waste water sludge, in which the fresh sludge is mixed with fermented sludge. In a reaction compartment a mixing funnel can be placed in such a position that the installation shows some resemblance to the installation according to the present invention.

However, in this device according to German Patent Specification No. 275,498 the fresh sludge is directed into the mixing funnel, flowing out of same at the bottom and is mixed with fermented sludge, and the ascending gas is substantially directed to the bottom of said funnel in order to improve the sludge mixing.

The invention is further explained with reference to the enclosed drawings, which represent a schematic view of the installations with devices according to the present invention, and which are given only by way of example and should not be regarded as a limitation.

In these drawings, the following is depicted:

FIG. 3 shows a longitudinal sectional view of another rectangular embodiment of the installation according to the invention, wherein a gutter channel is positioned in the centre of the after-settling compartment.

Figure 1:
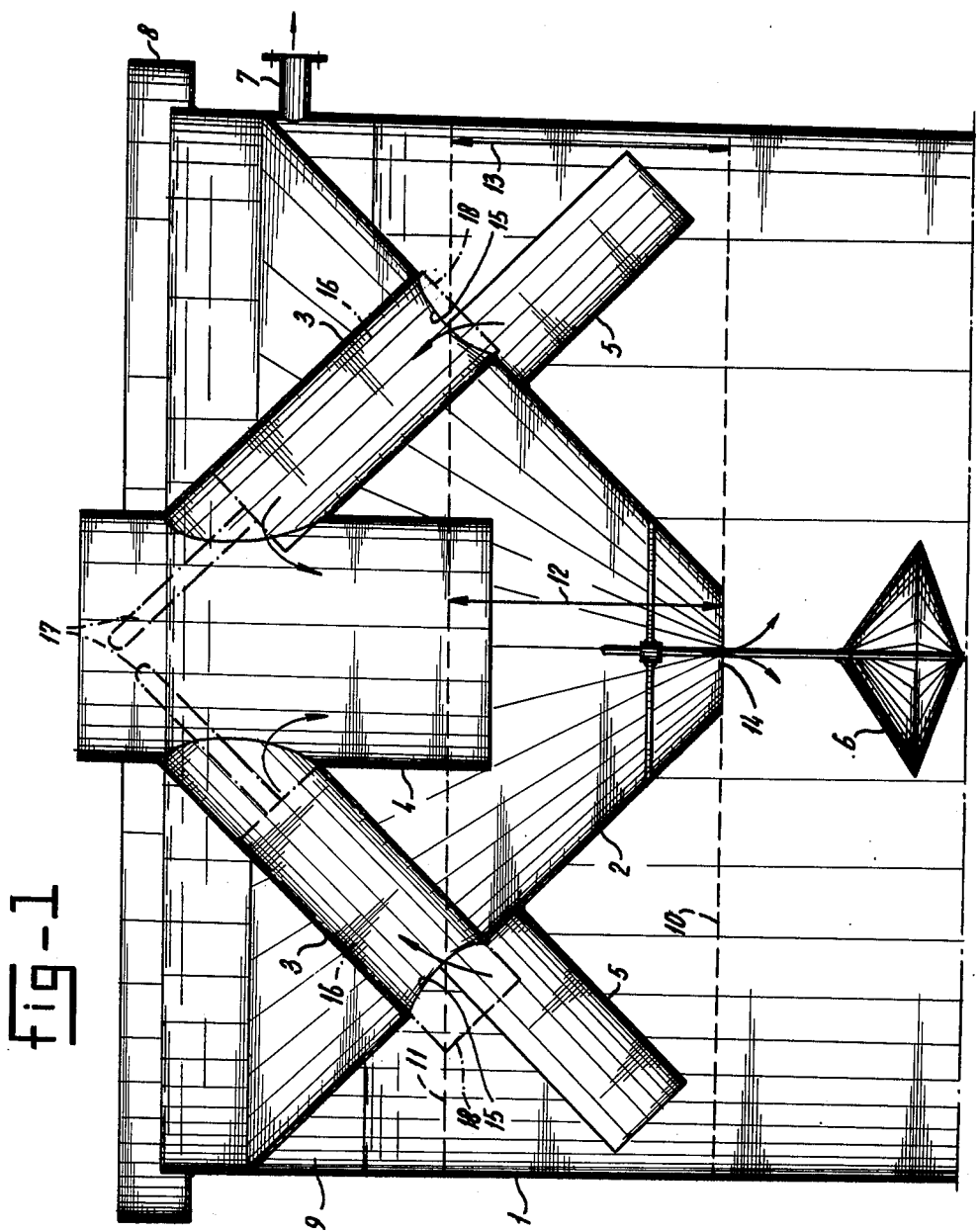
FIG. 1 shows a radial sectional view of a cylindrical installation which is an embodiment of the invention.

In these figures the following parts are shown:
1—reactor wall
2—wall of the after-settler
3—conducts forming the inlet openings into the after-settler
4—zone for collecting foam
5—bulkhead under inlet openings
6—bulkhead under outlet openings
7—gas conveyance
8—over flow drain
9—gas collecting zone
10,11—horizontal planes wherein between the liquid columns 12 and 13 are positioned
12—column of liquid in the after-settler with much sludge and without gas bubbles
13—column of liquid outside of the after-settler having less sludge but with gas bubbles The after-settling compartment in FIG. 1 has the shape of a circular funnel or knotted cone with an angle of slope of e.g. 45° having an opening 14 at its lower side. In said funnel openings 15 may be present at e.g. four positions, wherein the conducts 3, in this example cylindrical pipes, have been fixed. In FIG. 1 also for this item a slop angle of 45° has been selected such that the axle of the pipes is perpendicular to the wall ot said funnel. However, this is not obligatory for the function of the device. The four pipes 3 reach into the central zone 4 which is open at its lower and upper side.

Under each pipe 3 there is a bulkhead 5 e.g. consisting of a semi-cylindrical piece of pipe which prevents gas bubbles ascending to reach into the pipes 3, since said bubbles during said ascending are directed into a direction outside the reach of the openings 15 by means of the bulkhead shielding.

Under the opening 14 of the funnel a shape 6 is positioned, which is made of two conical parts. By this shape ascending gas bubbles are directed to the side outside the reach of the opening 14; also the recycling of the sludge from zone 2 into the reactor is directed in a controlled way.

The reactor zone 1 has not been depicted lower than the bulkhead 5, however, this zone is extending lower in a distance of 2 to 4 meters, viz. at least in a distance of the same height as that of the after-settling compartment 2. At the bottom of the reactor compartment there is an inlet for the waste water to be treated, which might be subjected to a prepurification, and furthermore there is an outlet for drawing off and cleaning of the installation; said outlet may be closed during normal function of the installation.

The function of the installation is as follows:

An amount of water with active sludge for anaerobic decomposition is fed into the reactor zone of the tank and continuously waste water to be purified is added. By the fermentation reaction gas bubbles are being formed in the sludge, and the sludge is gradually decomposed into methane and some carbon dioxide and water. The gas functions as a bubble pump, and around the after-settling compartment 2 an upward effect is carried out in the liquid. Thus said liquid is flowing with part of the sludge through openings 15 into the conducts 3 and therefrom into the foam collecting zone 4, where the foam is floating upon the liquid and may be removed either by skimming means or by separate (not depicted) overflow or by chemical agents. Water and sludge drop into the funnel of the after-settling compartment, and at the bottom of the funnel a higher concentration of sludge is effected. The mixture leaves the funnel 2 through opening 14.

The ascending gas bubbles do not flow with the liquid into the openings 15 but are directed with liquid around the shielding bulkhead 5, such that the liquid can reach said opening but the gas bubbles rise till the zone 9 wherefrom the gas is carried off through the gas exit 7 under a certain overpressure which is sufficiently high to have some gas remaining in the zone 9, in spite of the higher liquid level in the after-settling zone 2.

The circulation of the liquid and the sludge as described takes place mainly by the difference in specific gravity of the mixture of water sludge and gas bubbles in the zone between the level lines 10 and 11, i.e. over the column 12 within the after-settling compartment 2 and the column 13 outside of this compartment in the reactor. Within the after-settling compartment an ascending liquid flow is superposed upon said circulation movement, whereby the liquid in the foam collecting zone 4 flows downward and splits into two flow streams in the lower part; this results in a descending flow to the opening 14 with the thickening-in sludge and an ascending flow around the zone 4 to the overflow 8, and said flow is compensated by the waste water to be treated which is fed at the bottom of the installation.

The flow due to the overflow 8 will arrive in a zone which is gradually widening in a direction to the top, and thus the flow rate is decreasing, with the result that the liquid will be stripped of sludge particles in an efficient way.

Into the conduct pipes 3 inner pipes 16 may be telescoped, which may be pushed in the conduct pipes and back, in order to vary the height of the inlet openings 18 at their lower ends, such that an inherent circulation in the natural manner can be adjusted and controlled as described in the above.

During the sufficient fermentation as much sludge material is decomposed as fed with fresh waste water, such that substantially no removal of sludge material from the installation will be necessary, except for cleaning purposes of the device.

Figure 2:
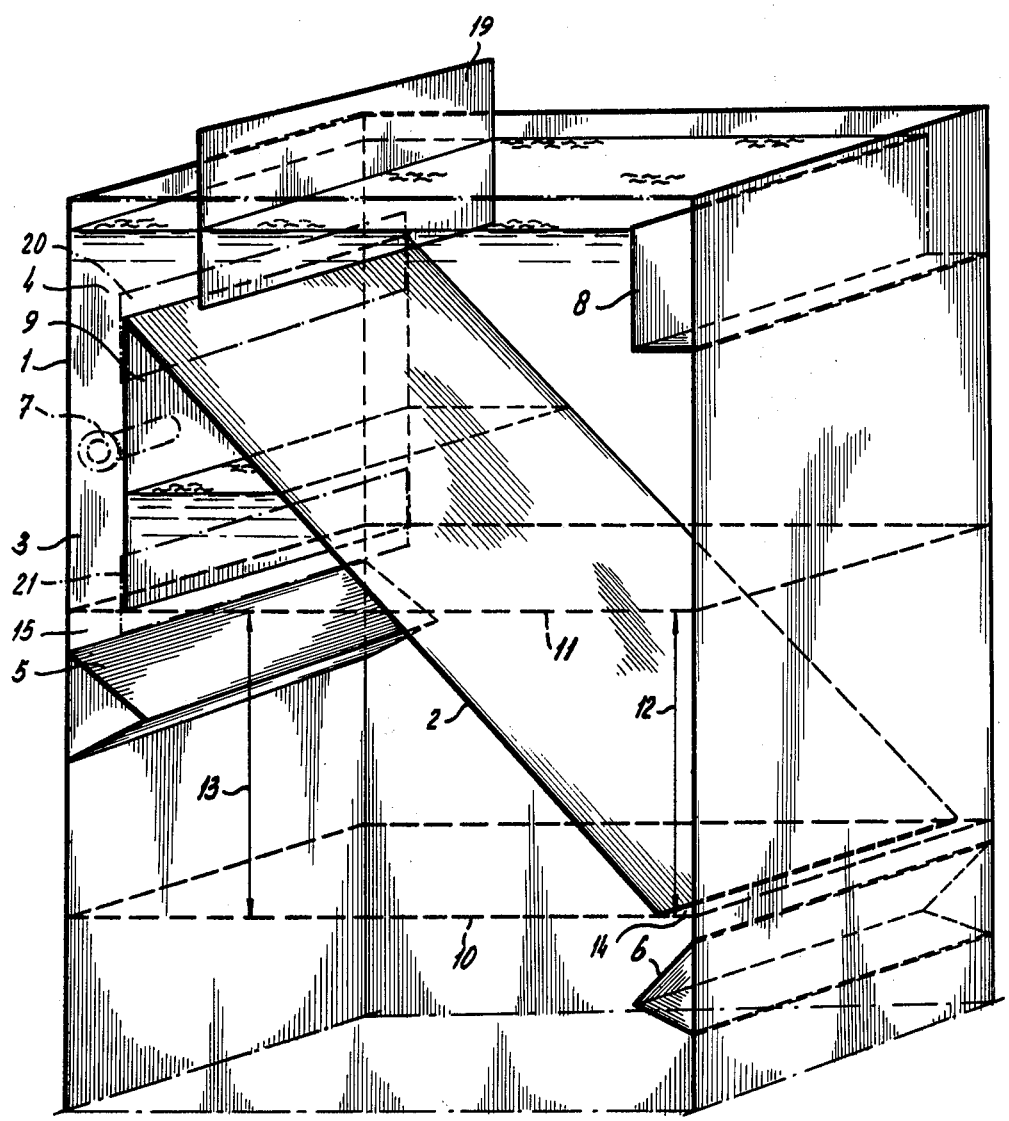
FIG. 2 shows a prespective view of a rectangular installation which is an embodiment of the invention.

In FIG. 2 a rectangular reactor tank is depicted; in this figure the front and back walls are omitted, as well as the lower part of the reactor tank, for a better understanding of the invention.

In said lower part of the reactor tank there is an inlet for the waste water with sludge to be treated, and this lower part is about as high as the part of the installation displayed.

In this embodiment as shown, the bulkheads 5 and 6 for directing the gas bubbles are made in the form of straight shaped beveled bodies of sheet material as shown in the drawing, said bulkheads shielding the rectangular openings 14 and 15 in top of them from ascending gas bubbles, such that said bubbles cannot reach the zone 9 and cannot ascend inside said openings 14 and 15. Another bulkhead 19 forms a separation between the surface of the foam collecting compartment 4 and the surface of the compartment from which the purified effluent is drained through the overflow gutter 8. Vertically adjustable bulkheads 20 and 21 are used for the control of the supply into the after-settling compartment and the removal from the reactor zone through opening 15.

In FIG. 3 two after-settling compartments 2 adjacent to each other are depicted, which may have either circular or rectangular horizontal sectional shapes. At the adjacent sides there are vertical conduct pipes 3, in the central part a mutual conduct pipe 3 for both after-settling compartments; further this installation is in principle substantially equal to that as shown in FIGS. 1 and 2.

Further to these embodiments other types can be constructed, wherein the use of the same principle as the above is applied, since said principle may be used for general applications in several different kinds of constructions of after-settling installations.

The following example is described for the understanding of one particular embodiment of such an installation according to the present invention.

EXAMPLE

In a cylindrically shaped reactor tank having a contents of 6 $m^3$ an after-settling device according to FIG. 1 had been assembled. The distance between both horizontal planes 10 and 11, which caused the effect of the sludge after-settling device, was 25 cm. Into this reactor sludge waste water was supplied at the sump of the tank with a rate of 1 $m^3$ per hour. The chemical oxygen demand (C.O.D.) of the supplied fluid was 3000 gram per $m^3$. The retention time was 4 hours.

Initially into this reactor a sludge had been supplied as a graft material from a sludge fermentation tank of a municipal waste water purification installation. After a short period of adaptation the amount of gas developed was 1 $m^3$ per hour comprising about 90% by volume of methane (natural gas).

The growth or increase of sludge was very small, which is inherent to anaerobic decomposition; it appeared to be practically possible to separate the sludge from the flow in such an efficient way that a concentration of 35 through 40 gram organic sludge material per liter fluid could be maintained in the reactor.

There were no disturbances in continuous operation, and the efficacy has been proven by the fact, that at a retention time of 4 hours of the liquid a retention time of the sludge material of 25 days was observed.

Thus, in a very economical way a purification of sludge waste water has been obtained by means of the installation according to the present invention, while methane had been recovered, which could be used as an energy source.

The purified water showed the properties as required by environmental authorities.

What applicants claim is as follows:

1. An installation for the anaerobic purification of a liquid effluent which comprises a reactor tank, an after-settler compartment located in the top part for settling and separating the sludge and liquid, means for introducing the liquid effluent in the reactor tank and means for separating the gases from said sludge and liquid, said after-settler compartment comprising an inlet opening for the mixture of sludge and liquid from the reactor tank and an outlet opening to recycle said sludge and liquid to said reactor tank, said outlet opening being positioned at a level lower than said inlet opening, first deflecting means serving as shield for said inlet opening and second deflecting means for said outlet opening to and from said after-settling compartment respectively positioned in the reactor tank so that the upward flow of developed gases is kept away from said openings, separate interception compartment and outlet means for said gases, the bottom of the after-settling compartment being inclined downwardly towards said outlet opening to allow sludge settled therein to move to said outlet opening by its own weight, said first deflecting means being positioned at a level higher than said outlet opening to allow the gas generated by the anaerobic fermentation in the reactor tank to entrain liquid and sludge while rising in the reactor tank outside the after-settling compartment up to said first deflecting means.

2. An installation as claimed in claim 1, wherein said inlet opening to said after-settling compartment has an horizontal projection, said first deflecting means is a bulkhead, which is positioned below said inlet opening, said bulkhead directing the gases sideward from the horizontal projection of said inlet opening into the interception compartment for said gases, while the liquid with sludge flows around said bulkhead into said inlet opening.

3. An installation as claimed in claim 2, wherein on top of said bulkhead a vertical channel is positioned, a substantially vertical wall of which ends at its upper end in an overflow to the after-settler compartment, said wall delimiting, together with the wall of said after-settler compartment, and beneath of said overflow, said interception compartment for the gases, which is connected with an outlet for the gases under overpressure.

4. An installation as claimed in claim 1 wherein said second deflecting means is a second bulkhead, said outlet opening is located in the sump of said after-settler compartment, said outlet opening is positioned over said second bulkhead, said second bulkhead preventing the ascending gas bubbles to reach said outlet opening.

5. The installation according to claim 4 wherein said second bulkhead is made of two conical portions.

6. The installation according to claim 4 wherein said first and second bulkheads are beveled bodies.

7. An installation as claimed in claim 1 wherein the after-settler compartment widens upwardly and has at its upper inner end a compartment for collecting foam which is open at its lower end, and which is delimited by a raised border, into which one or several pipes protrude, which pipes extend from the wall of the after-settling compartment in an oblique direction upwardly to said raised border, thus forming inlet openings for introducing the mixture of sludge and water into the after-settler compartment.

8. An installation as claimed in claim 7 which comprises adjustable means to vary the height of said inlet opening for the mixture of sludge and liquid into said after-settler compartment.

9. An installation as claimed in claim 8, wherein one or several pipes are longitudinally movable telescopically in order to vary the height of the inlet opening of the reactor zone into the after-settler compartment at the end of said pipes which protrude into said reactor zone.

10. An installation as claimed in claim 9, wherein the telescopically movable pipes are pushed in fixed pipes which extend from the wall of the after-settler compartment to the raised border of the compartment for interception of foam.

11. An installation as claimed in claim 1 wherein said reactor tank has a rectangular horizontal section and said after-settler compartment is delimited by a single oblique bulkhead extending entirely between two opposite walls of said reactor tank, said bulkhead constituting said first and second deflecting means, an inlet opening to the after-settling compartment is located at one end of said bulkhead and an outlet opening from the after-settler compartment is present at the other end of said bulkhead.

12. An installation as claimed in claim 1 wherein in the upper end of the reactor tank at least two after-settler compartments are positioned.

* * * * *